United States Patent

Moggi

[11] 4,062,865
[45] Dec. 13, 1977

[54] PROCESS FOR THE SYNTHESIS OF SUBSTITUTED INDOLENINES

[75] Inventor: Pietro Antonio Moggi, Milan, Italy

[73] Assignee: Snamprogetti S.p.A., Milan, Italy

[21] Appl. No.: 565,132

[22] Filed: Apr. 4, 1975

[30] Foreign Application Priority Data

Apr. 5, 1974  Italy .................................. 50203/74

[51] Int. Cl.² .......................................... C07D 209/04
[52] U.S. Cl. ...................... 260/319.1; 260/326.12 R; 260/326.16; 260/429.9; 260/566 R
[58] Field of Search .................... 260/319.1, 326.12 R, 260/326.16, 326.12

[56] References Cited

U.S. PATENT DOCUMENTS

3,671,214  6/1972  Alt ...................................... 260/319.1

OTHER PUBLICATIONS

Garry, M., Annales de Chimi, vol. 17, pp. 61–97; pertinent pp. 66–72 (Jan.–June 1942).
Elderfield, Heterocyclic Compounds, vol. 3, pp. 22–35 (1952).
Houlihan, "Indoles," part one, pp. 317–375; pertinent pp. 319 and 324–326 (1972).
Sundberg, "The Chem. of Indoles," p. 168 (1970).

*Primary Examiner*—Ethel G. Love
*Attorney, Agent, or Firm*—Ralph M. Watson

[57] ABSTRACT

A process for the preparation of substituted indolenines of the formula:

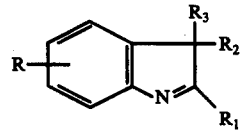

wherein R is hydrogen, alkyl, aryl or cycloalkyl, halogen, or a functional group selected from among cyano, hydroxyl, alkoxy, nitro or sulphonic groups, and wherein $R_1$, $R_2$ and $R_3$ are the same, or different, and are selected from alkyl, aryl or cycloalkyl radicals, comprising reacting in the presence of an organic solvent an aromatic amine of the formula:

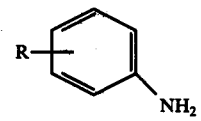

with a tertiary hydroxyketone of the formula:

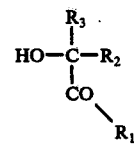

wherein R, $R_1$, $R_2$ and $R_3$ have the same meanings as defined above, in the presence of a catalyst selected from mineral acids, organic acids, Lewis acids or ionic exchange resins in acid form, and wherein said aromatic amine is slightly in excess, to form first an imine of the formula:

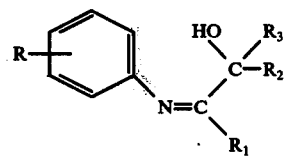

under reaction conditions wherein the solvent is removed by azeotropic distillation, and thereafter continuing the reaction to remove water and cyclizing to the desired indolenines. In a preferred embodiment, 2,3,3-trimethylindolenine is prepared by reacting an excess of aniline with 3-methyl-3-hydroxybutan-2-one in the presence of $ZnCl_2$ as catalyst utilizing benzene as solvent. The substituted indolenines obtained are useful in production of dyes and other compounds useful in the dyeing and photographic industries.

20 Claims, No Drawings

PROCESS FOR THE SYNTHESIS OF SUBSTITUTED INDOLENINES

BACKGROUND OF THE INVENTION

1. Field of the Invention:

The present invention relates to a novel process for the synthesis of substituted indolenines having the following general formula

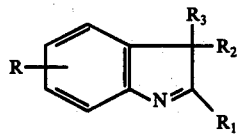

in which R is hydrogen, alkyl, aryl cycloalkyl, halogen, or a functional group selected among cyano hydroxyl alkoxy nitro or sulphonic groups, $R_1$ and $R_2$ and $R_3$, are the same or different, and are alkyl, aryl or cycloakyl radicals.

A particularly known substituted indolenine is 2,3,3-trimethylindolenine, which is an important synthesis intermediate in the dyeing and photographic product industry.

For example, starting from 2,3,3-trimethylindolenine or from 1,3,3-trymethyl-2-methylindolenine which is obtained therefrom through methylation and following alkalinization of the reaction medium, it is possible to obtain, by reacting with the suitable reactants, dyes for natural and synthetic fibers containing, as the characteristic chromophore, the methynic group —CH=CH— or the azamethynic group —CH=N—, and various products employable in the photographic field, as dyes, spectral sensitizers and as organic photoconductors in electrophotography.

2. Prior Art 2,3,3-trimethylindolenine up until now has been prepared, analogously to other substituted indolenines, only through the Fisher synthesis, starting from phenylhydrazine and methylisopropylketone, or through a methylation of alkylated indoles, for instance from 2,3-dimethylindole which can be obtained, through the Fisher synthesis, from phenylhydrazine and methylethylketone. Thus, in the past the desired substituted indolenines were prepared using processes which employed very expensive starting materials and difficult procedures.

SUMMARY OF THE INVENTION

The present invention relates to a process for the preparation of substituted indolenines through reactions which can be simply and easily carried out from starting materials available or obtainable according to known methods.

More particularly the inventive process is carried out by condensing an aromatic amine with a tertiary hydroxyketone to give an imine which, in the same reaction vessel and under suitable conditions, is cyclized through a removal of water.

The process of the present invention is illustrated schematically in the following diagram wherein a substituted aniline is reacted with a tertiary hydroxyketone as shown.

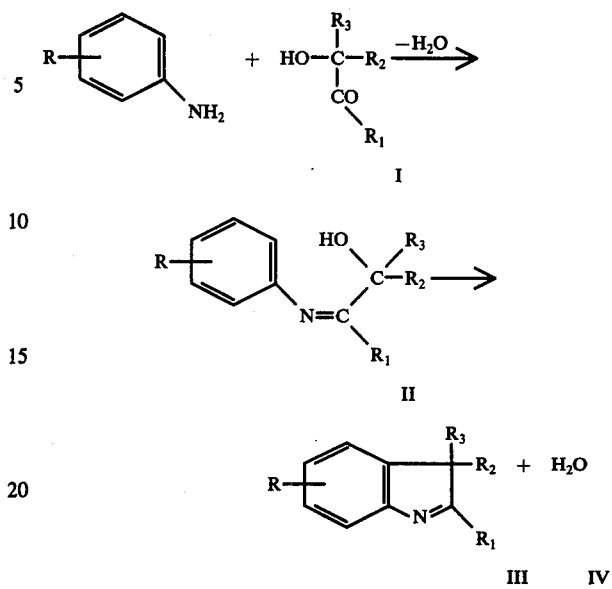

In the foregoing reaction, R, $R_1$, $R_2$ and $R_3$ have the same meanings as previously defined.

Thus, by way of example in the case of 2,3,3-trimethylindolenine, it is obtained from aniline and 3-methyl-3-hydroxybutan-2-one which, in turn, may be prepared from 3-methylbutyn-1-olo-3 according to known methods.

The condensation between aromatic amine and hydroxyketone is preferably carried out in presence of an excess of amine of up to about a 2:1 molar ratio of amine to the hydroxyketone.

A preferred way for carrying out the above process consists in performing the condensation under a reflux of a solvent capable of removing, by an azeotropic distillation, the water which is formed in the reaction, the solvent is preferably selected from among the aromatic hydrocarbons. Additionally, the reaction is preferably carried out in the presence of a catalyst selected from among mineral acids, organic acids, Lewis acids or ion-exchange resins in acid form. A preferred use is particularly made of $ZnCl_2$ or complexes thereof with an aromatic amine, which is prepared separately or formed in the reaction vessel itself.

Then, after the distillation of the solvent, the reaction is completed by continuing the reflux treatment of amine until water formation is observed. The operative details will be more evident from examination of the following examples which, are illustrative only and are not to be considered restrictive of the invention which is defined in the appended claims.

As abovesaid, starting hydroxyketone can be obtained according to methods known in the scientific papers, such as, for instance, the hydration of acetylenic alcohols in the presence of mercury salts and sulphuric acid as catalysts.

ILLUSTRATIVE EMBODIMENTS

Example 1

200 cc of xylene, 90 cc (~ 1 mole) of aniline and 2 cc of $H_3PO_4$ at 85% are added to 100 cc (~ 1 mole) of 3-methyl-3-hydroxybutan-2-one (MHBK). The mixture is heated till to boil, water being removed from the reaction by an azeotropic distillation while xylene refluxed in the distillation column. When the water had been completely collected, both the aqueous phase obtained by separating the azeotrope and the organic phase in the vessel were subjected to chromatographic analysis.

In all, a 73.8% conversion of MHBK is determined together with a 57.9% selectivity to 2,3,3-trimethylindolenine.

Example 2

70 g of anhydrous $ZnCl_2$ dust are added a flask containing 1000 cc of aniline and refluxed over 2 hours. At the end the solution is cooled; a crystalline solid is obtained, which is filtered and washed with xylene, then dried in an oven under vacuum at 70° C. At the end 148 g of a solid are recovered in the form of shiny needle crystals, whose composition agrees, on the base of the elementary analysis, with the formula $ZnCl_2.(C_6H_5NH_2)2$ : C 44.0%(44.7); H 4,3%(4.3; N 8.7%(8.7); Cl 22.4%(22.0); Zn 20.6%(20.3).

The yield with respect to the $ZnCl_2$ employed is 90% of the theoretical value.

Example 3

300 cc of benzene, 180 cc (~ 2 moles) of aniline and 4.5 g of the complex $ZnCl_2.(C_6H_5NH_2)_2$ prepared according to Example 2 are added to 100 cc (~ 1 mole) of MHBK and the whole refluxed while water is removed by azeotropic distillation.

After 4 hours of refluxing the conversion of MHBK is about 80%. For, the reaction products, the selectivity to 2,3,3-trimethylindolenine is only 3%, 95% being constituted by the imine produced by the simple condensation of aniline and MHBK, i.e. N-[(αβ-dimethyl-β-hydroxy) n.propyliden] aniline

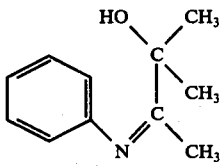

At this point benzene and unreacted MHBK are distilled, then the mixture is reflux boiled over 4 hours at the boiling temperature of aniline; at the end of treatment the selectivity to 2,3,3-trimethylindolenine in the reaction products is raised to 92%, while that of the intermediate imine is reduced to 0.2%. The mixture is cooled and then distilled under vacuum in order to recover excess aniline; 2,3,3-trimethylindolenine is then obtained as overhead product (boiling point 74°–75° C at 4–5 mmHg) at 99.3% purity.

Example 4

1000 cc of xylene, 920 g (9.90 moles) of aniline and 20 g (0.06 moles) of the complex $ZnCl_2$.aniline prepared according to Example 2 are added to a solution containing 515 g (5.04 moles) of MHBK in 400 g of $H_2O$, derive from the hydration of 3-methyl butyn-1-olo-3. Use is made of distilling apparatus having a 10 plate column, and the operation carried out so that the overhead product constituted by the azeotrope water-xylene (temperature of about 95° C) is recovered and then separated in a separator. The overhead fraction is actually constituted by a ternary azeotrope water-xylene-MHBK, which separates into two phases; the aqueous one containing 13,9% and the xylenic one containing 2.2% MHBK.

According to this procedure, 123 g (1.21 moles) of MHBK are distilled. Then the solution is refluxed in xylene over 4 hours, and the distillation again carried out. A fraction consisting of xylene is separated and then under vacuum, a fraction consisting of aniline (564 g = 6.06 moles) at 99% purity; at end 2,3,3-trimethylindolenine (420 g = 2.64 moles) at 98% purity is recovered as overhead product (boiling point 74°–75° C at 4.5 mmHg). The yield in 2,3,3-trimethylindolenine, calculated with respect to unrecovered MHBK, is 69%.

Example 5

1.5 1 of benzene, 900 cc (920 g; 9.90 moles) of aniline and 20g (0.06 mole) of the complex $ZnCl_2$-aniline prepared according to Example 2 are added to a solution containing 515 g (054 mole) of MHBK in 600 cc of water. The whole is refluxed for 2 hours and then the azeotrope water-benzene distilled and separated in a separator while benzene is refluxed in the column. 720 cc of an aqueous phase are separated thereby, containing about 1.5% MHBK (10.8 g = 0.11 mole).

After the removal, by distillation, of benzene too, the mixture is completely refluxed in aniline for 4 hours. In this phase, water is again formed which is passed overhead as an azeotrope and collected through an aromatic system acting on the refluxing device, applied by a temperature control at the column head. In this phase 70 cc of $H_2O$ are collected.

The system is then cooled and distilled under vacuum (~ 10 mmHg) so that, at head, a fraction is first separated constituted by aniline at 99% (416 = 4.47 moles); and then 2,3,3-trimethylindolenine at 99.3% purity, boiling at 105° C at 12 mmHg (745 g = 4.68 moles). The overall yield in 2,3,3-trimethylindolenine is respectively 92.8% with respect to MHBK and 86% with respect to aniline consumed during the process.

In the following Example there are reported the results of some tests showing the possibility of broadening the inventive process to the synthesis of various 2,3,3-trimethylindolenine derivatives.

Example 6

According to the same procedure of Example 5, the catalyst being $ZnCl_2$, the following derivatives of 2,3,3-trimethylindolenine are prepared (between the brackets there are the yields with respect to MHBK) : 7-methyl (78%); 5-chloro (72%); 5-hydroxy (61%); 5-methoxy (74%); 5-nitro (64%).

What I claim is:

1. A process for the preparation of an indolenine of the formula:

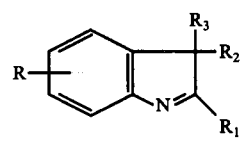

wherein R is hydrogen, alkyl, aryl, cycloalkyl, halogen, or a functional group selected from among cyano, hydroxyl, alkoxy, nitro and sulphonic groups; each of $R_1$, $R_2$ and $R_3$ are the same, or different, and are alkyl, aryl, or cycloalkyl, comprising reacting an aromatic amine of the formula:

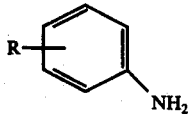

wherein R is the same as in formula IV, in an organic solvent, with a tertiary hydroxyketone of the formula:

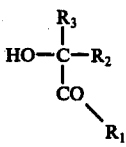

wherein $R_1$, $R_2$ and $R_3$ are as defined in formula IV, to form an imine of the formula:

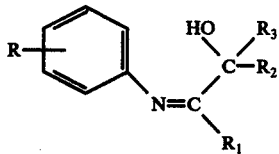

wherein $R_1$, $R_2$ and $R_3$ are as defined in formula IV and removing water from said imine to cyclize it to form the indolenine of formula IV.

2. A process as claimed in claim 1 wherein there is present a catalyst selected from among mineral acids, organic acids, Lewis acids, and ion exchange resins in acid form.

3. A process as claimed in claim 1 wherein said aromatic amine is present in a molar excess in relation to said tertiary hydroxyketone of up to 2:1.

4. A process as claimed in claim 2 wherein said process is carried out under reflux of the solvent to form an azeotropic mixture with water.

5. A process as claimed in claim 2 wherein said catalyst is zinc chloride.

6. A process as claimed in claim 4 wherein said solvent is removed by said azeotropic distillation and the process continued under amine reflux until formation of water is observed.

7. A process as claimed in claim 2 wherein said aromatic amine is present in a molar excess in relation to said tertiary hydroxyketone of up to 2:1.

8. A process as claimed in claim 7 wherein said solvent is an aromatic hydrocarbon.

9. A process as claimed in claim 8 wherein said solvent is benzene.

10. A process as claimed in claim 7 wherein said catalyst is zinc chloride.

11. A process as claimed in claim 10 wherein an aromatic amine is aniline.

12. A process as claimed in claim 7 wherein said tertiary hydroxyketone is 3-methyl-3-hydroxybutan-2-one.

13. A process as claimed in claim 10 wherein said tertiary hydroxyketone is 3-methyl-3-hydroxybutan-2-one.

14. A process as claimed in claim 12 wherein amine is aniline.

15. A process as claimed in claim 12 wherein said aromatic amine is aniline and the product obtained is 2,3,3-trimethylindolenine.

16. A process as claimed in claim 12 wherein said aromatic amine is o-toluidine and the product obtained is 2,3,3,7-tetramethylindolenine.

17. A process as claimed in claim 12 wherein said aromatic amine is p-chloroaniline and the product obtained is 2,3,3-trimethyl-5-chloroindolenine.

18. A process as claimed in claim 12 wherein said aromatic amine is p-hydroxyaniline and the product obtained is 2,3,3-trimethyl-5-hydroxyindolenine.

19. A process as claimed in claim 12 wherein amine is p-anisidine and the product obtained is 2,3,3-trimethyl-5-methoxyindolenine.

20. A process as claimed in claim 12 wherein said aromatic amine is p-nitroaniline and the product obtained is 2,3,3-trimethyl-5-nitroindolenine.

* * * * *

UNITED STATES PATENT AND TRADEMARK OFFICE
CERTIFICATE OF CORRECTION

PATENT NO. : 4,062,865
DATED : December 13, 1977
INVENTOR(S) : Pietro Antonio Moggi It is certified that error appears in the above-identified patent and that said Letters Patent are hereby corrected as shown below:

Column 1, line 21, After "groups," insert --and--.
Column 2, lines 1 to 24, Formulae are incorrectly numbered and should appear --

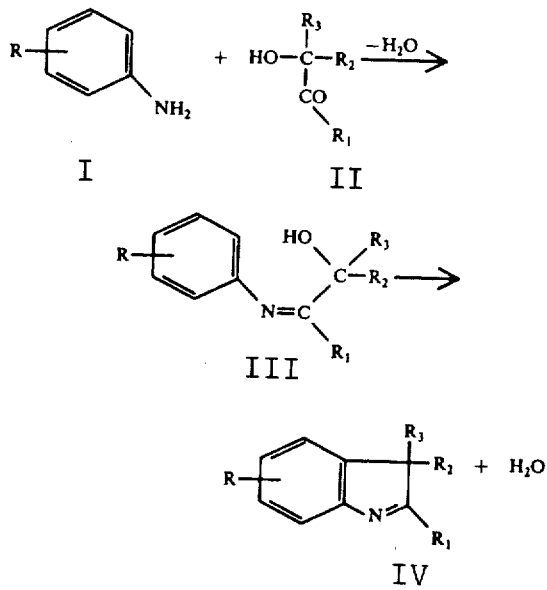

-- .

Signed and Sealed this

Second Day of May 1978

[SEAL]

Attest:

RUTH C. MASON
Attesting Officer

LUTRELLE F. PARKER
Acting Commissioner of Patents and Trademarks